000A

United States Patent [19]

Young et al.

[11] Patent Number: 5,772,660
[45] Date of Patent: Jun. 30, 1998

[54] TROCAR ASSEMBLY WITH ELECTROCAUTERY PENETRATING TIP

[75] Inventors: Wayne P. Young, Brewster, N.Y.; Dominick L. Mastri, Bridgeport; Darryl S. Pereira, Monroe, both of Conn.

[73] Assignee: United States Surgical Corporation, Norwalk, Conn.

[21] Appl. No.: 834,085

[22] Filed: Apr. 14, 1997

Related U.S. Application Data

[63] Continuation of Ser. No. 407,342, Mar. 20, 1995, abandoned.

[51] Int. Cl.⁶ .................................................. A61B 17/36
[52] U.S. Cl. .............................. 606/42; 606/34; 606/37; 604/164
[58] Field of Search ..................... 606/32–52; 604/154, 604/158, 164

[56] References Cited

U.S. PATENT DOCUMENTS

| | | |
|---|---|---|
| 4,535,773 | 8/1985 | Yoon . |
| 4,601,710 | 7/1986 | Moll . |
| 5,104,382 | 4/1992 | Brinkerhoff . |
| 5,116,353 | 5/1992 | Green . |
| 5,152,754 | 10/1992 | Plyley et al. . |
| 5,226,426 | 7/1993 | Yoon . |
| 5,290,243 | 3/1994 | Chadorow et al. . |
| 5,290,304 | 3/1994 | Storace . |
| 5,295,993 | 3/1994 | Green . |
| 5,318,580 | 6/1994 | Gresl, Jr. . |
| 5,417,687 | 5/1995 | Mardella ................................. 606/32 |

*Primary Examiner*—David M. Shay

[57] ABSTRACT

A trocar which automatically deactivates upon penetration through a body wall includes a housing portion, an obturator shaft mounted with respect to the housing portion and having proximal and distal ends, a conductor element extending at least partially along the obturator shaft for conducting energy from an energy source and a conductive tip member associated with the distal end of the obturator shaft for penetrating tissue. The conductive tip member is mounted for movement relative to the obturator shaft between a first position in communication with the conductor element and a second position disassociated from the conductor element.

27 Claims, 9 Drawing Sheets

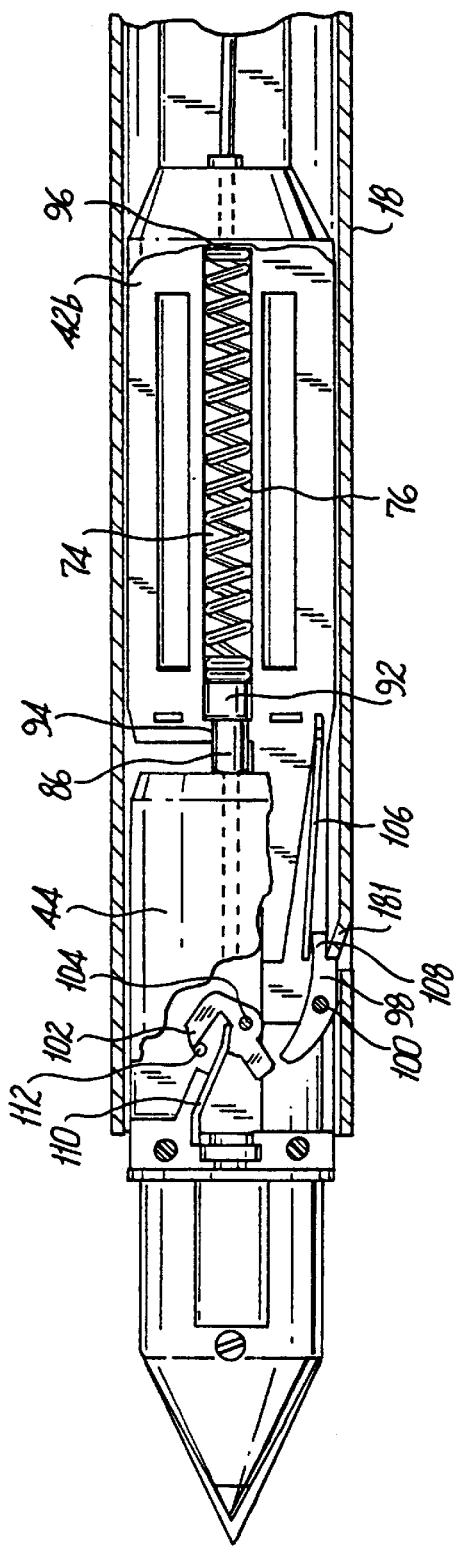
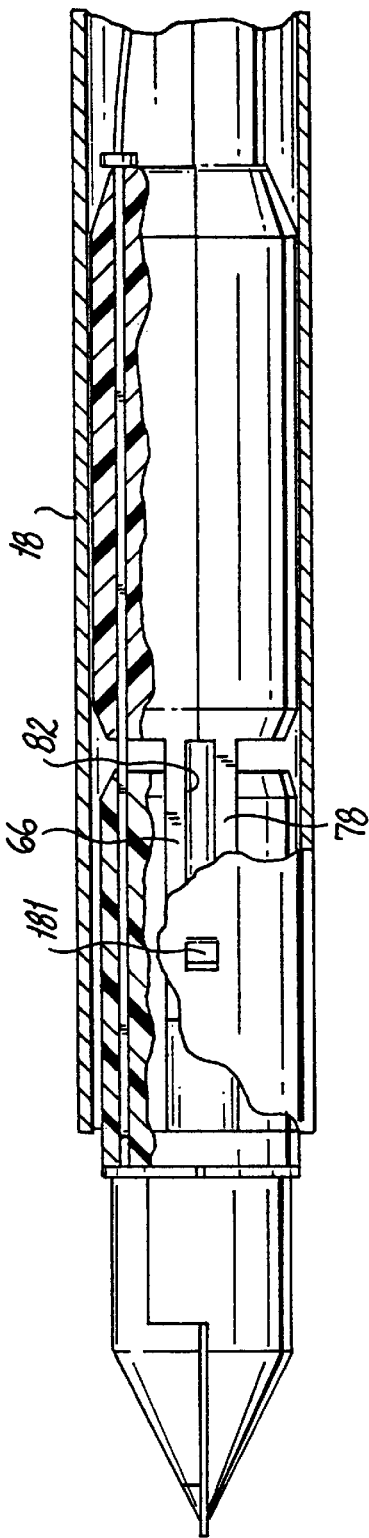
Fig. 4
Fig. 7

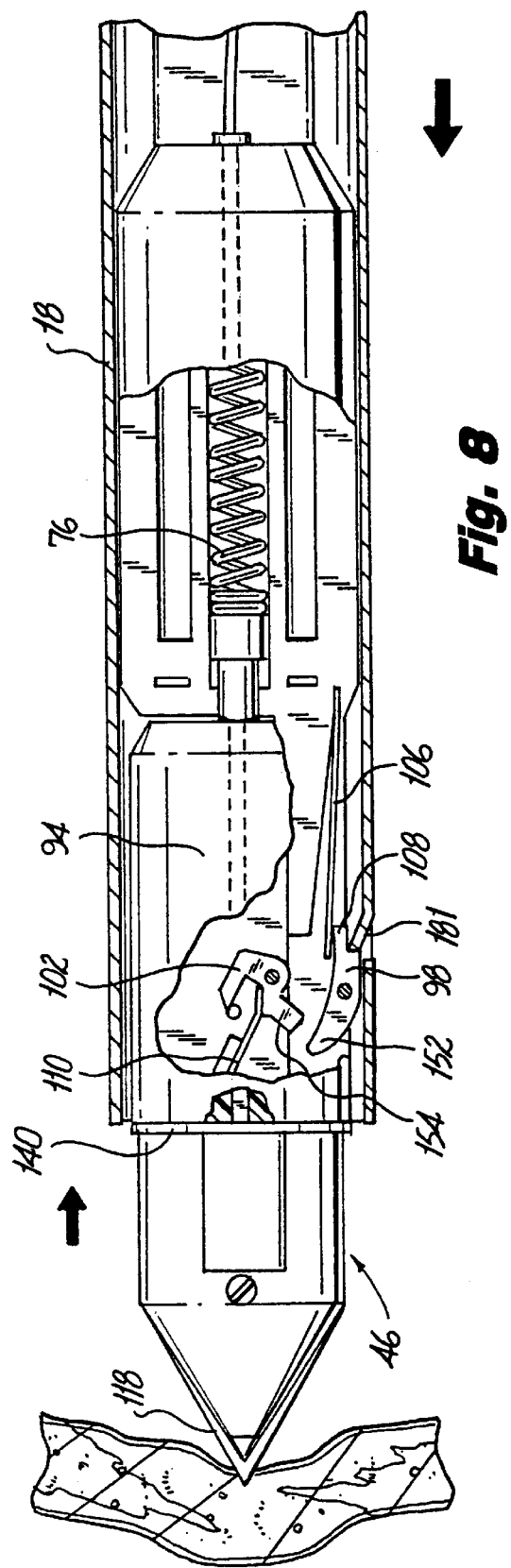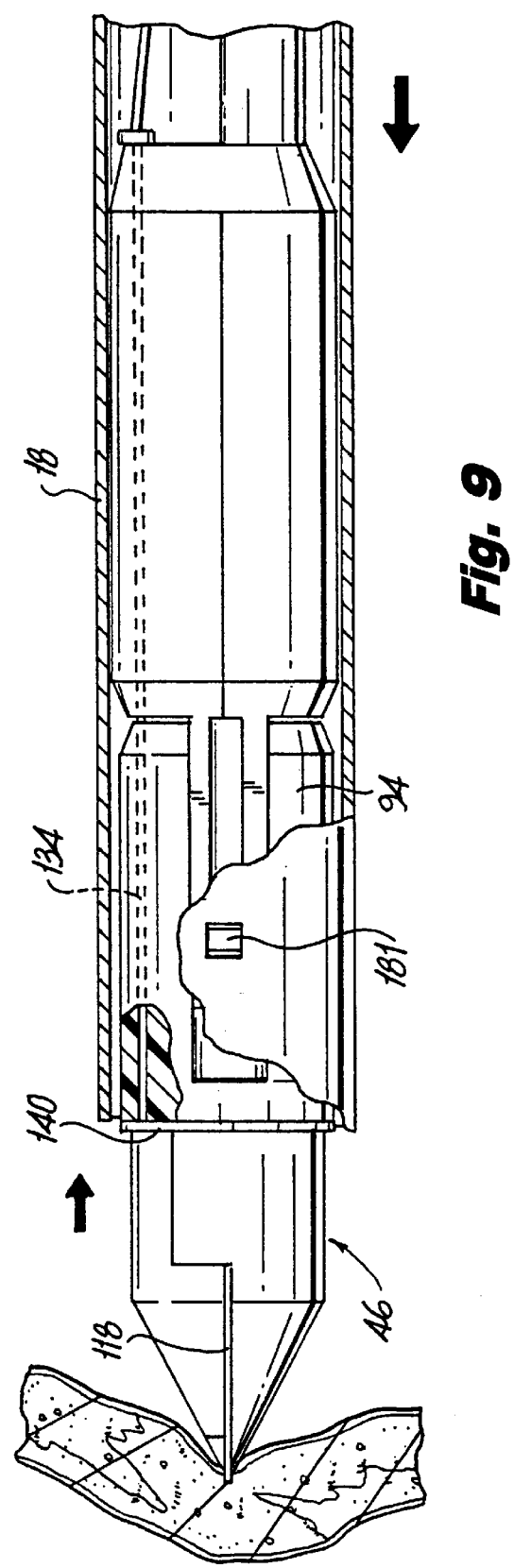

TROCAR ASSEMBLY WITH ELECTROCAUTERY PENETRATING TIP

This is a continuation of copending application Ser. No. 08/407,342, filed on Mar. 20, 1995.

BACKGROUND

1. Field of the Disclosure

The present disclosure relates generally to trocar assemblies for use in endoscopic surgical procedures and, in particular, to a trocar assembly having an electrocautery penetrating tip which automatically deactivates upon entry into a body cavity.

2. Description of the Related Art

Endoscopic surgical procedures, that is, surgical procedures performed through tubular sleeves or cannulas, have been increasingly accepted as the preferred treatment for ailments traditionally treated via conventional surgical techniques. Initially, endoscopic surgical procedures were primarily diagnostic in nature. More recently, however, as endoscopic technology has advanced, surgeons are performing increasingly complex and innovative surgical procedures using endoscopic principles. In endoscopic procedures, surgery is performed in any hollow viscus of the body through a small incision or through narrow endoscopic tubes (cannulas) inserted through small entrance wounds in the skin. Endoscopic procedures require the surgeon to act on organs, tissues and vessels far removed from the incision, thereby requiring that any instruments to be used in such procedures be sufficient in size and length to permit remote operation.

Laparoscopic surgery is a type of endoscopic surgery in which the surgical procedures are performed in the interior of the abdomen. In accordance with laparoscopic techniques, the surgical region, e.g., abdominal cavity, is insufflated with a gas such as $CO_2$ to raise the cavity wall away from the internal organs therein. Thereafter, a trocar is used to puncture the body cavity. Generally, a trocar includes an obturator having a sharp penetrating tip disposed within a protective tube or sleeve. The trocar is typically used with, or incorporates, a cannula sleeve which remains within the incision subsequent to removal of the obturator. The cannula defines a port for the insertion of surgical instruments required to perform the desired surgery. An example of a known trocar is described in commonly assigned U.S. Pat. No. 4,601,710 to Moll.

Recent developments in the design of surgical trocars include the provision of an electrocautery cutting element to thereby reduce the force required to penetrate the body tissue, e.g., the abdominal or peritoneal lining. For example, one conventional electrocautery trocar incorporates an electrosurgical wire routed through the obturator tip. The electrosurgical wire is energized to cause cutting and penetration through the body tissue resulting in a precisely formed incision in the skin tissue and the underlying peritoneal lining.

One of the significant disadvantages of the above described electrocautery trocar and other known trocars incorporating electrosurgical cutting implements is that deactivation of the electrosurgical current is manually controlled by the user at the proximal end. Thus, the cutting implement remains energized until the surgeon deactivates the instrument. Consequently, a potential exists for the energized piercing element to contact underlying viscera and other body structures after penetration through the abdominal wall, thereby increasing trauma to the patient and patient recovery time.

SUMMARY OF THE INVENTION

Accordingly, the present disclosure relates to a trocar which automatically deactivates upon penetration through a body wall. The trocar includes a housing portion, an obturator shaft mounted with respect to the housing portion and having proximal and distal ends, a conductor element extending at least partially along the obturator shaft for conducting energy from an energy source and a conductive tip member associated with the distal end of the obturator shaft for penetrating tissue. The conductive tip member is mounted for movement relative to the obturator shaft between a first position in communication with the conductor element and a second position disassociated from the conductor element. In the first position, the conductive tip member is used to penetrate the body cavity. The conductive tip member assumes its first position upon application thereof against body tissue. The trocar may further include a biasing member, e.g., a spring member, for biasing the conductive tip member to the second position disassociated from the conductor element.

In a preferred embodiment, the trocar includes an obturator sleeve mounted to the housing portion and extending distally therefrom. The obturator shaft is reciprocally axially movable within the obturator sleeve between a first position wherein the conductive tip member is contained within the obturator sleeve and a second position wherein the conductive tip member is at least partially disposed beyond the obturator sleeve. The trocar may further include means for releasably maintaining the obturator shaft in its second position. The preferred release means includes a latch mechanism having a latch member mounted to the shaft and being engageable with the obturator sleeve. The latch mechanism also includes a pawl member which is engageable with the latch member to move the latch member to a position disengaged from the obturator sleeve. The pawl member is preferably configured enlarged and dimensioned to engage the latch member to move the latch member to its disengaged position upon movement of the conductive tip member from the first position thereof to the second position thereof.

BRIEF DESCRIPTION OF THE DRAWINGS

Preferred embodiments of the disclosure are described hereinafter with reference to the drawings wherein:

FIG. 4 is a side view in cross-section of the obturator portion illustrating the latch mechanism for releasably retaining the obturator portion in the extended position;

FIG. 7 is a side view in partial cross-section of the obturator portion of the trocar of FIG. 1 in an extended position with the obturator tip extending beyond the obturator sleeve;

FIG. 8 is a view similar to the view of FIG. 4 illustrating the obturator tip applied against tissue and the resulting proximal movement of the extension member and the obturator tip to activate the electrocautery system;

FIG. 9 is a view similar to the view of FIG. 7 further illustrating proximal movement of the trocar tip and the movement of the latch mechanism;

DETAILED DESCRIPTION OF THE PREFERRED EMBODIMENTS

Figure 1:
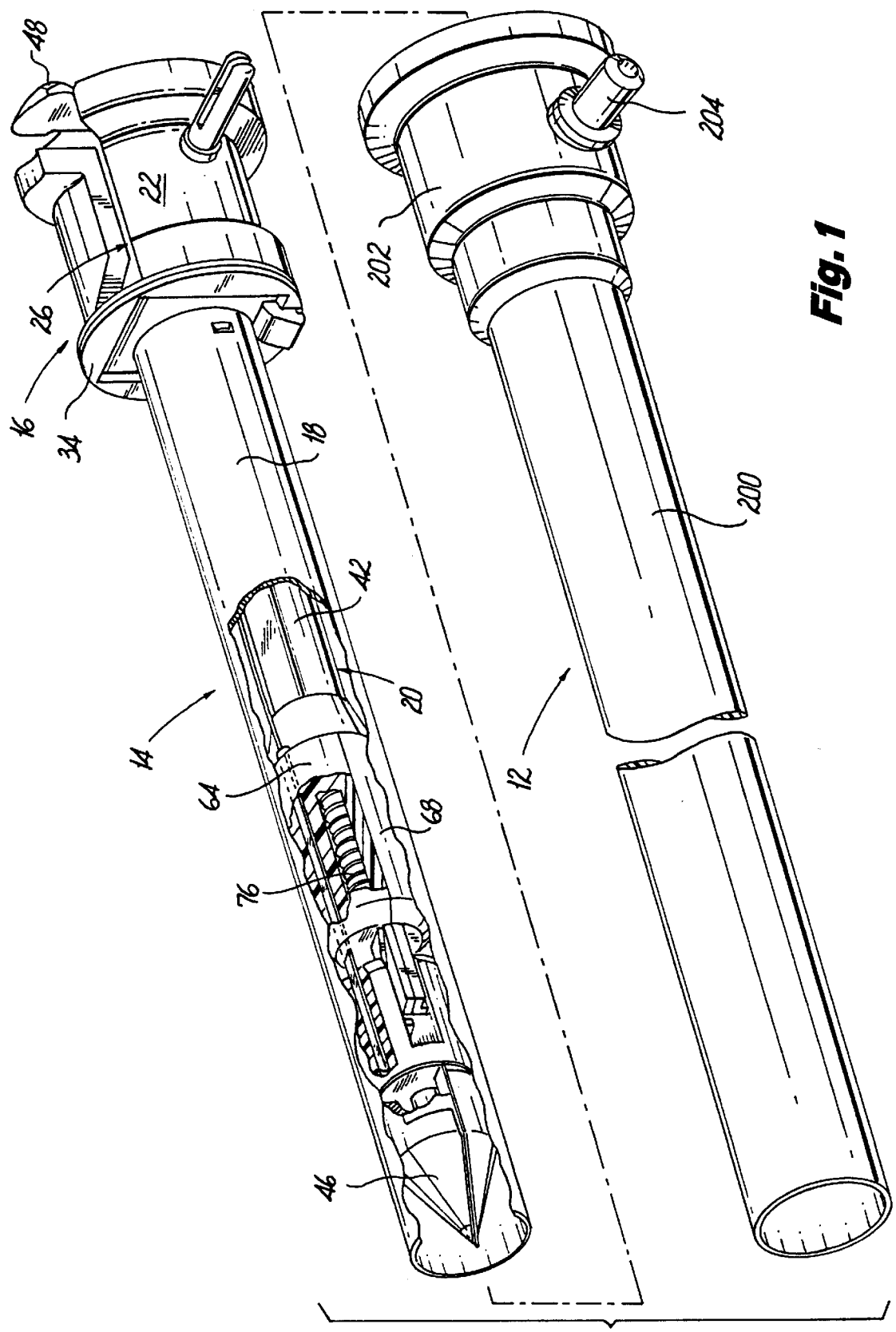
FIG. 1 is a perspective view with portions cut-away of the trocar assembly of the present invention including an obturator assembly and a cannula assembly.

Referring now in specific detail to the drawings, in which like reference numerals identify similar or like components throughout the views, FIG. 1 illustrates in perspective view the electrocautery trocar assembly constructed according to the principles of the present disclosure. The trocar assembly 10 is intended to be used in laparoscopic surgery where insufflation gases are introduced into the peritoneal cavity to raise the cavity wall away from the internal organs therein. Trocar assembly 10 includes a cannula assembly 12 and an obturator assembly 14 which is positionable within the cannula assembly 12. The term "obturator assembly" as used herein refers to the tissue penetrating portion of the trocar assembly 10.

Figure 2:
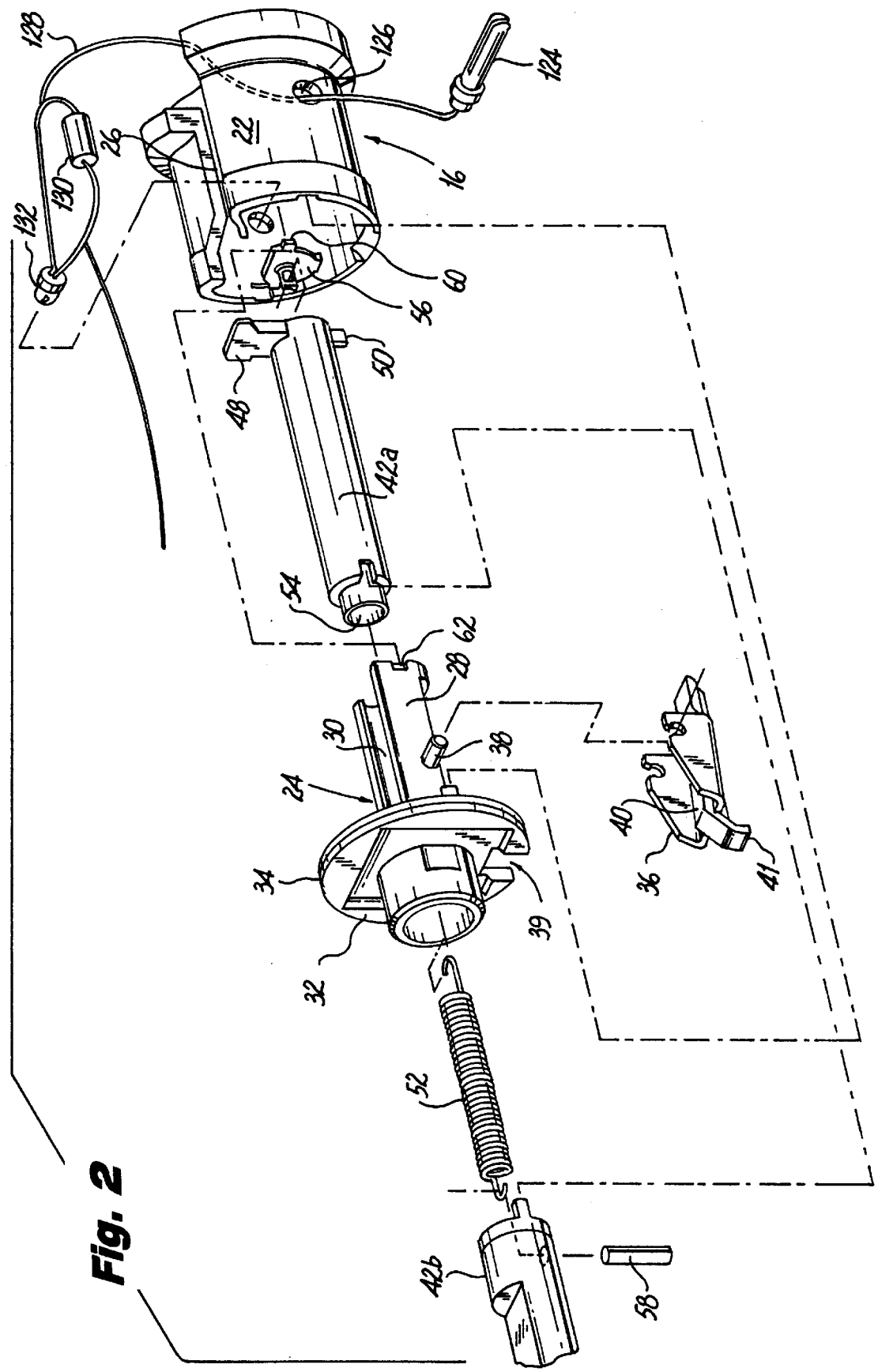
FIG. 2 is a perspective view with parts separated of the housing portion of the obturator assembly of FIG. 1.

Referring now to FIGS. 1 and 2, obturator assembly 14 will be discussed in detail. Obturator assembly 14 is similar to the safety trocar disclosed in commonly assigned U.S. Pat. No. 5,116,353 to Green, the contents of which are incorporated herein by reference. Obturator assembly 14 includes housing 16, obturator sleeve 18 extending distally from the housing 16 and obturator portion 20 disposed within sleeve 18. Housing 16 includes frame 22 which is advantageously configured to be grasped by the hands of the user and an insert member 24 positioned within the frame 22. Frame 22 is preferably manufactured from a suitable rigid material such as polymeric materials, steel, aluminum or the like and includes an axial slot 26 formed in its outer wall surface. Insert 24 includes proximal insert portion 28 defining channel 30 and distal insert portion 32 having circumferential flange 34. In the assembled condition of housing 16 shown in FIG. 1, circumferential flange 34 of insert 24 is affixed to the distal surface of frame 22 with suitable means such as adhesives, cements, etc.

Obturator assembly 14 further includes a latch lock 36 which is pivotally mounted about two opposed pivot pins 38 extending radially outwardly from insert 24. Latch lock 36 is at least partially accommodated within rectangular groove or recess 39 formed in circumferential flange 34 and defines an inner inclined surface 40. Latch lock 36 includes a locking ledge 41 which is uniquely configured to engage corresponding structure of cannula assembly 14 to detachably mount the obturator assembly 14 to the cannula assembly 12 as will be described hereinbelow.

Figure 3:
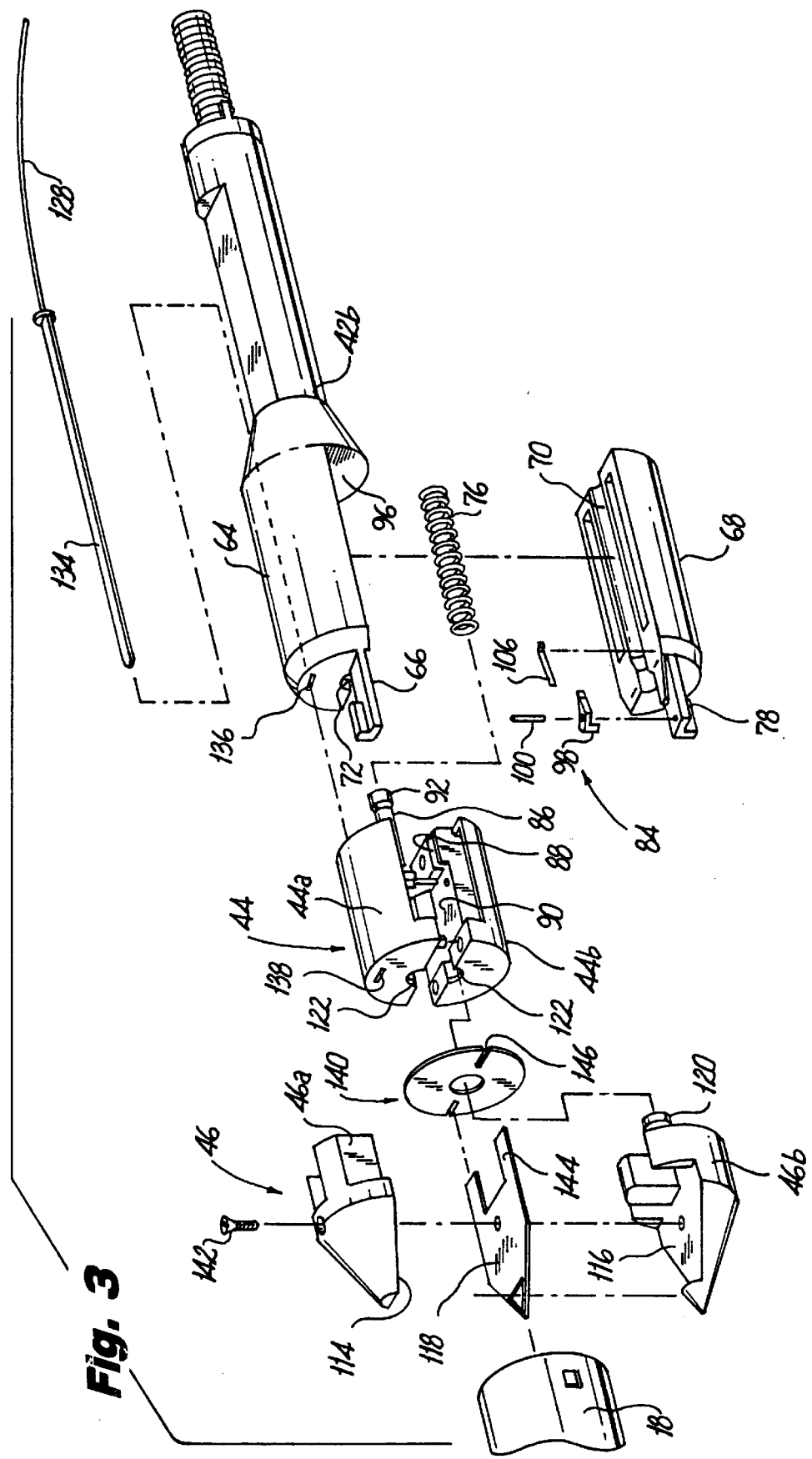
FIG. 3 is a perspective view with parts separated of the tissue penetrating portion of the obturator assembly of FIG. 1.

Referring now to FIG. 1, in conjunction with FIGS. 2 and 3, obturator portion 20 of obturator assembly 14 includes an obturator shaft 42 having rear shaft portion 42a and forward shaft portion 42b which is shown in FIG. 2 and FIG. 3 respectively, an extension member 44 mounted to the distal end of forward shaft portion 42b and obturator tip 46. Rear shaft portion 42a is accommodated within channel 30 of insert 24. As illustrated in FIG. 2, rear shaft portion 42a includes a trigger finger 48 extending transversely relative to the longitudinal axis of obturator portion 20. Trigger finger 48 is accommodated within axial slot 26 of housing 16 and is reciprocally moveable within the slot 26 to effectuate "arming" and "disarming" of the trocar. Trigger finger 48 defines a lower portion 50 which extends beyond the lower surface of rear shaft portion 42a in contact with inner surface 40 of latch lock 36. Lower portion 50 of trigger finger 48 rides along the inner surface 40 of lock latch 36 during distal movement of trigger finger 48 to cause the latch lock 36 to pivot into locking engagement with the cannula assembly 12 as will be discussed below.

Referring still to FIGS. 1–3, and particularly FIG. 2, obturator portion 20 further includes an extension spring 52 at least partially accommodated within a bore 54 defined in rear shaft portion 42a. Extension spring 52 is connected at its proximal end to spring stud 56 and at its distal end to spring mounting pin 58 which is connected to rear shaft portion 42b as best shown in FIG. 2. Spring stud 56 is mounted to the rear end surface of insert 24 and includes two diametrically opposed tabs 60 which are received within correspondingly dimensioned recesses 62 formed in the insert 24 to facilitate such mounting. In the assembled condition, extension spring 52 extends through channel 30 of insert 24 and within longitudinal bore 54 of rear shaft portion 42a to fixedly join obturator shaft 42 to housing 16 subject to the extension and retraction of extension spring 52.

Referring now to FIG. 1, in conjunction with FIGS. 3 and 4, forward shaft portion 42b includes a hemispheric distally extending arm 64 having an extension portion 66 extending therefrom. A corresponding hemispherically-shaped cover 68 is adapted to mount onto hemispheric arm 64 to define a substantially tubular configuration of substantially identical cross-section. A semi-circular channel 70 (FIG. 3) is formed in the inner surface of hemispheric cover 68. Similarly, a corresponding semi-circular channel 72 is formed in the inner surface of hemispheric arm 64. In the assembled condition of hemispheric arm 64 and hemispheric cover 68, the respective semi-circular channels 70, 72 define a tubular bore 74 within forward shaft portion 42b to accommodate compressor spring 76 as depicted in FIG. 4.

As best illustrated in FIG. 3, hemispheric cover 68 further includes a forward extension portion 78 extending distally therefrom. Extension portion 78 is slightly recessed relative to the inner surface of hemispheric cover 68. Consequently, in the assembled condition of hemispheric arm 64 on hemispheric cover 68, a recess or slot 82 is defined between the respective extension portions 66, 78 as depicted in FIG. 7. Slot 82 accommodates a latch mechanism identified generally as reference numeral 84 in FIG. 3.

Referring again to FIGS. 1, 3 and 4, extension member 44 includes upper and lower half sections 44a, 44b and a tubular mounting portion 86 extending from the proximal end of the upper half section 44a. Upper and lower half sections 44a, 44b each include a correspondingly dimensioned recess 88 formed on their inner surfaces 90 which respectively accommodates forward extending portions 66, 78 of hemispheric arm 64 and hemispheric cover 68 in the assembled condition of the instrument. With specific reference to FIG. 4, tubular mounting portion 86 is at least partially accommodated within tubular bore 74 formed in forward shaft portion 42b and defines an enlarged head 92 which engages a restricted portion 94 of bore 74 to mount the extension member 44 to the obturator shaft 42. Tubular portion 86 reciprocally moves within tubular bore 74 to permit reciprocal movement of the extension member 44 relative to obturator shaft 42. Compression spring 76, which is disposed within tubular bore 74 of obturator shaft 42, engages at its first end enlarged head 92 of tubular mounting portion 86 and at its second end abutment surface 96 of obturator shaft 42 to normally bias extension member 44 in the distal direction.

Referring to FIGS. 3 and 4, latch mechanism 84 serves in retaining obturator portion 20 in the armed position during penetration through the body tissue. Latch mechanism 84 also serves in releasing the obturator portion 20 upon penetration through the tissue to thereby disarm the obturator portion. Latch mechanism 84 includes latch 98 which is rotatably mounted to forward extension portion 78 of hemispheric cover 68 about pin 100 and pawl 102 (FIG. 4) which is mounted to the extension member 44 about pivot pin 104. A lever spring 106 is mounted to hemispheric cover 68 and engages the latch 98 in a manner to bias the rear engaging surface 108 of the latch 98 radially outwardly. A lever spring 110 is mounted to extension member 44 in a manner to engage pawl 102 and bias the pawl 102 to rotate in a general counterclockwise direction in reference to FIG. 4. An upwardly extending stop pin 112 provides a rotational stop to prevent pawl 102 from rotating in the counterclockwise direction. The operation of latch mechanism 84 will be discussed in further detail below.

Referring now to FIGS. 1, 3 and 4, obturator tip 46 includes lower and upper half sections 46a, 46b mounted to each other. Lower and upper half sections 46a, 46b have inner surfaces 114, 116 respectively which are strategically dimensioned to accommodate electrocautery cutting blade 118. A tubular mounting portion 120 extends proximally from lower half section 46b and is rotatably mounted within matching semicircular collar portions 122 defined in upper and lower half sections 44a, 44b of extension member 44. Thus, obturator tip 46 and cutting blade 118 are capable of rotating relative to extension member 44 and obturator shaft 42.

Referring now to FIGS. 2–3, the electrocautery system of obturator assembly 14 will be described. The electrocautery system includes contact 124 mounted within a correspondingly dimensioned aperture 126 formed in frame 22 and having a lead wire 128 connected thereto. Lead wire 128 is electrically connected to a tangent voltage suppressor 130 and an indicator light 132. Tangent voltage suppressor 130 may be a DC coupling capacitor which functions in suppressing spurious signals from passing through to the electrocautery cutting blade 118. Indicator light 132 indicates when the cutting blade 118 is energized. The electrocautery system also includes an in-line conducting rod 134. Conductor rod 134 is disposed within correspondingly dimensioned bores 136, 138 respectively formed in forward shaft portion 42b of obturator shaft 42 and extension member 44. A conductive washer 140 is mounted about tubular portion 120 of obturator tip 46 and is disposed between extension member 44 and the obturator tip 46. As previously mentioned, cutting blade or knife 118 is positioned between upper and lower half sections 46a, 46b of obturator tip 46 and is fixably connected to the obturator tip 46 through mounting pin 142. Conductive knife 118 includes two proximal leg portions 144 which are received within correspondingly dimensioned slots 146 formed in conductive washer 140 to electrically connect the two components.

Referring again to FIG. 1, cannula assembly 12 of trocar assembly 10 will now be described. Cannula assembly 12 includes cannula sleeve 200 and cannula housing 202 mounted on one end of the sleeve. Sleeve 200 defines a cannula passage in its interior for reception of obturator assembly 14 and may be formed of stainless steel or the like. Cannula housing 202 is rigidly secured to the proximal end of sleeve 200 and defines a longitudinal bore for reception and passage of obturator portion 20 of assembly 14. The proximal end portion of cannula housing 202 defines a generally circular cross-section similar in dimension to that of frame 22 of obturator assembly 14. Cannula housing 202 further includes an inner peripheral ledge (not shown) at its proximal end which cooperates with latch lock 36 of obturator assembly 14 to securely mount the obturator assembly to the cannula assembly 12 as will be described. Cannula housing 202 may further include a seal (not shown) to minimize loss of insufflation gases during introduction and removal of the surgical instrument through the cannula assembly 12. A stop cock valve 204 is also provided to permit the passage of insufflation gases through the cannula and into the body cavity.

Operation

Figure 5:
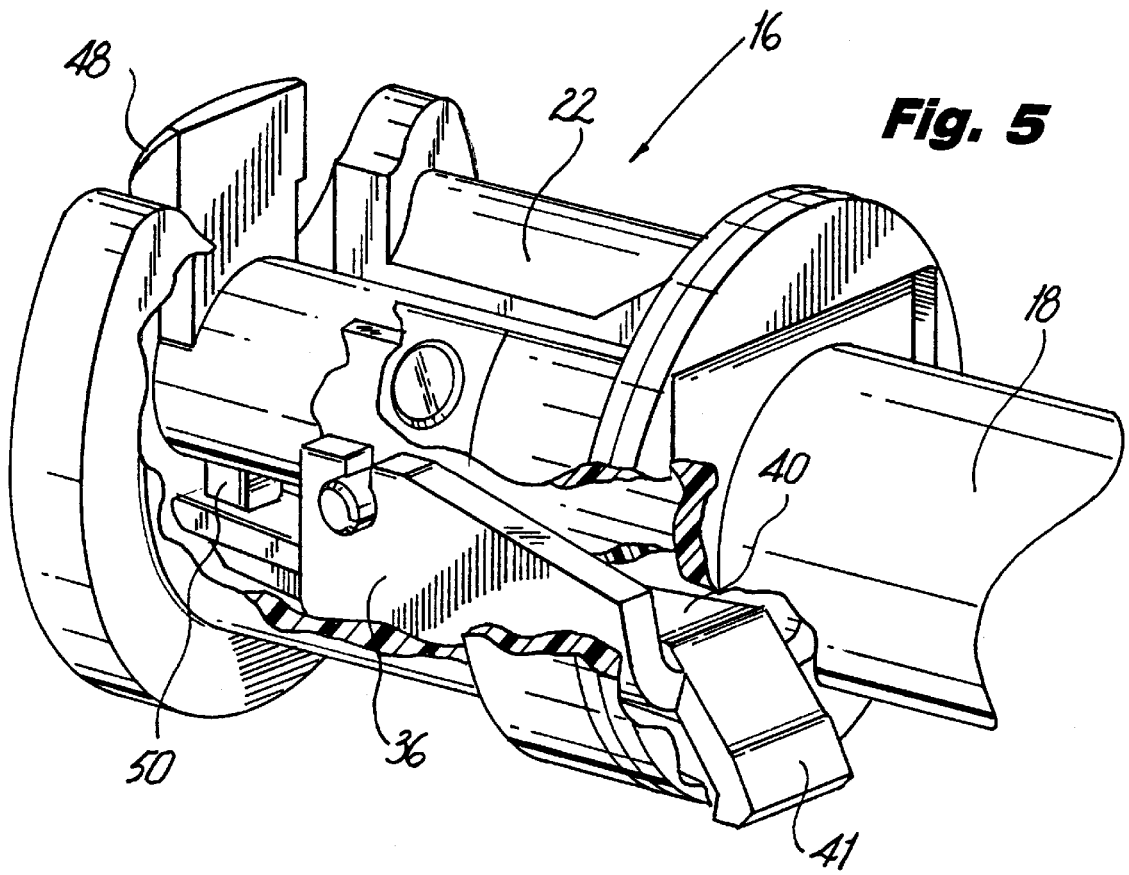
FIG. 5 is an enlarged perspective view with portions cut-away of the housing portion of the obturator assembly illustrating the manually operable finger in the proximal position.
Figure 6:
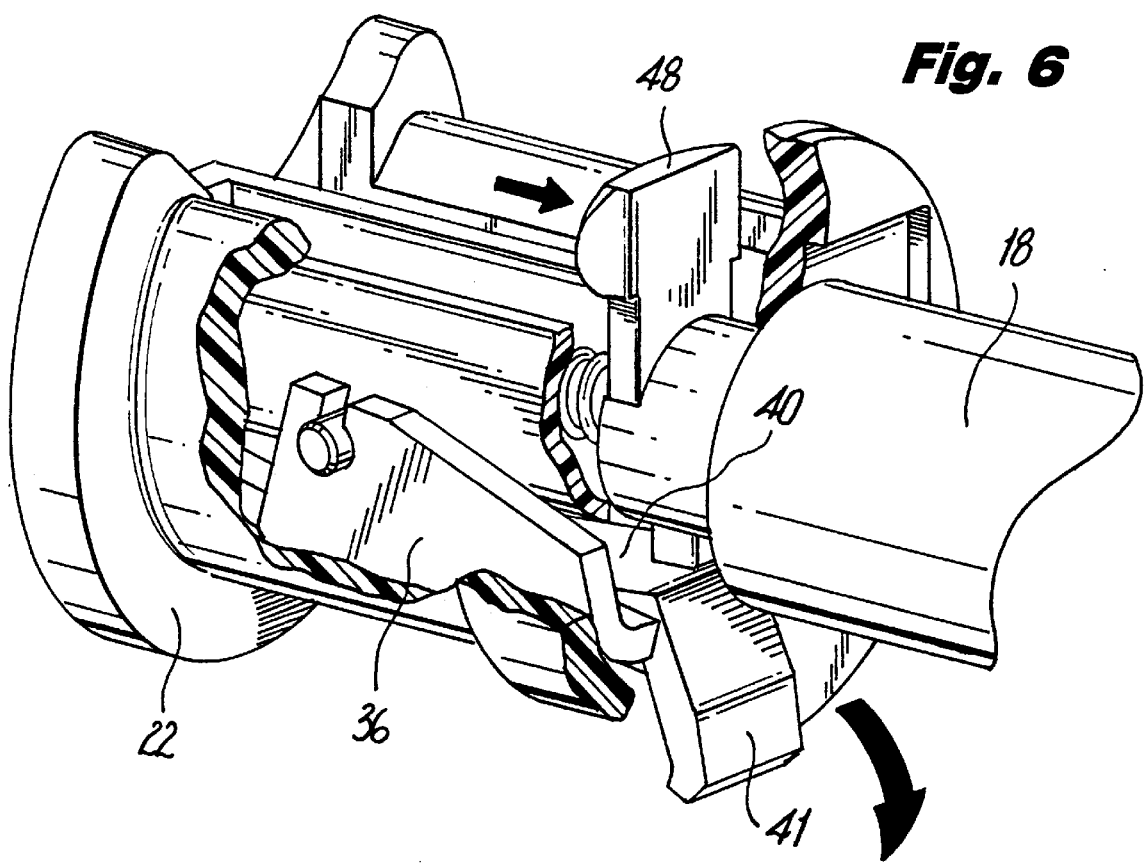
FIG. 6 is a view similar to the view of FIG. 5 illustrating the manually operable finger in the distal position corresponding to extension of the obturator tip beyond the obturator sleeve.

The operation of trocar assembly 10 will now be discussed. Referring to FIG. 1, obturator assembly 14 is positioned within cannula assembly 12 and advanced within the cannula assembly until cannula housing 202 is received within frame 22 of obturator housing 16. Referring now to FIGS. 5–6, with the obturator assembly 14 positioned within cannula assembly 12, trigger finger 48 of obturator assembly 14 is distally advanced from the position shown in FIG. 5 to the position shown in FIG. 6 to "arm" the trocar, i.e., to distally advance obturator shaft 20 so as to expose obturator tip 46 beyond the distal ends of both obturator sleeve 18 and cannula sleeve 200. During the advancing movement of trigger finger 48, the lower portion 50 of the trigger finger 38 traverses inner inclined surface 40 of the latch lock 36 to bias the locking ledge 41 of the latch lock 36 radially outwardly (in the direction of the arrow of FIG. 6). In the radial outward position, the locking ledge lockingly engages an inner peripheral ledge of cannula housing 202 thereby securing the obturator assembly 14 to cannula assembly 12.

The advancing movement of obturator shaft 20 also places extension spring 52 (FIG. 2) in tension, thereby biasing obturator shaft 20 and obturator tip 46 proximally, i.e., to the position in which obturator tip 46 is disposed within obturator sleeve 18. AS shown in FIGS. 4 and 7, however, such proximal movement of obturator shaft 20 is prevented by contact between the rear engaging surface 108 of latch 98 and internal shelf 181 defined within obturator sleeve 18. As noted above, lever spring 106 biases the rear engaging surface 108 of latch 98 into engagement with internal shelf 181.

Referring now to FIGS. 8–9, with the trocar tip in the armed position, the surgeon presses electrocautery conductive knife 118 against the body tissue. The force exerted by conductive knife 118 on the tissue forces obturator tip 46 and extension member 44 in the proximal direction (as indicated by the directional arrow) against the influence of compression spring 76. As extension member 44 moves proximally, the forward portion 152 of latch 98 engages the lower leg 154 of pawl 102 thereby causing the pawl to rotate in a general clockwise rotation against the bias of lever spring 110 so as to gain clearance thereby. As soon as pawl 102 clears latch 98, the pawl 102 rotates in a counterclockwise direction to its initial rest position under the influence of lever spring 110 and against stop pin 112 as shown in FIG. 8.

In addition, as obturator tip 46 and extension member 44 move proximally, conductive washer 140 of the electrocautery system is also moved proximally into contact with electrical conducting rod 134 thereby energizing the washer 140 and conductive knife 118. Thus, in this position, the trocar is used to penetrate the body tissue with electrocautery cutting blade 118. It is to be noted that during activation of conductive knife 118, indicator light 132 mounted to obturator housing 16 is illuminated.

Figure 10:
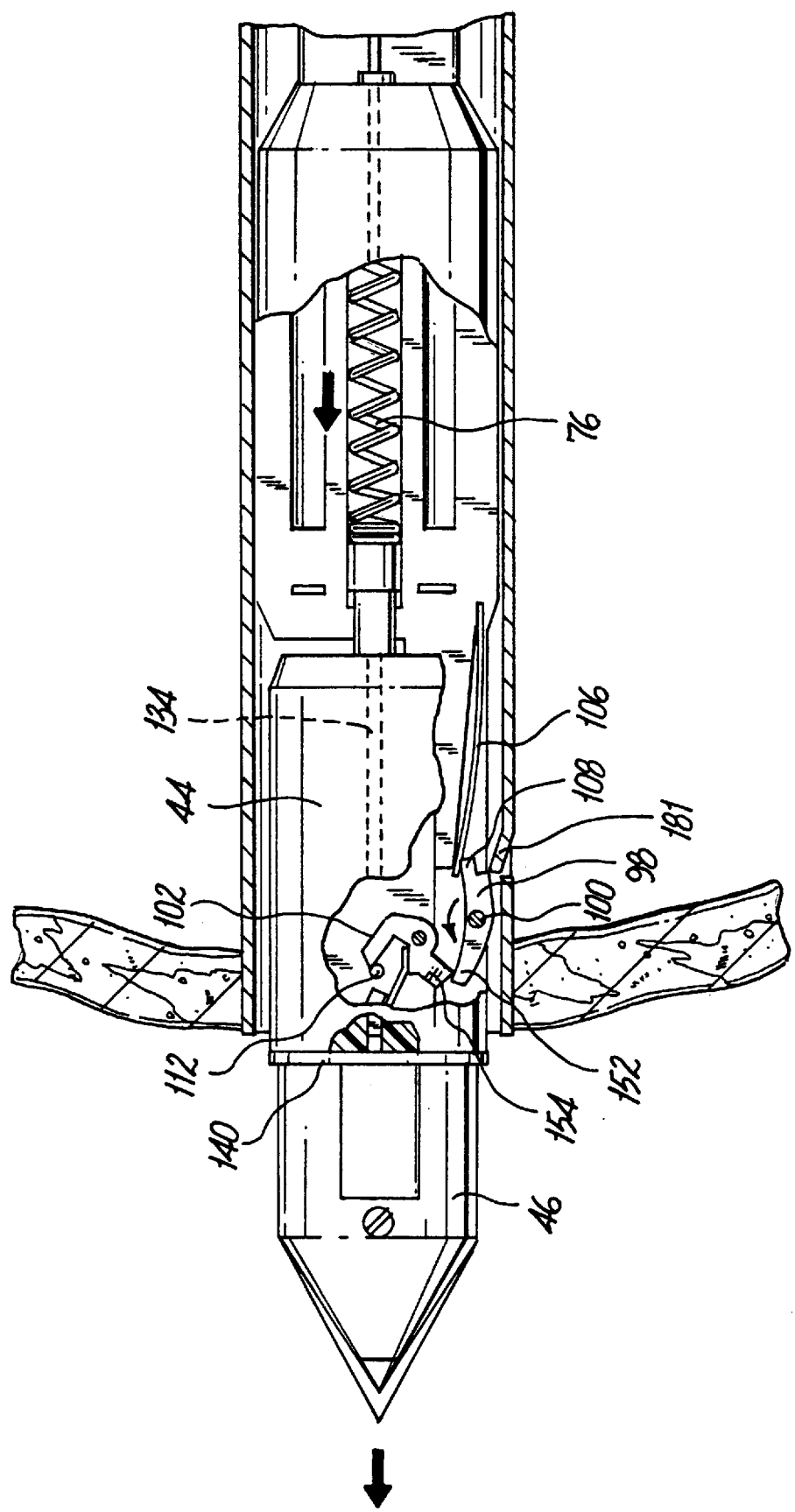
FIG. 10 a side view in cross-section of the obturator portion illustrating the trocar tip penetrating through the tissue to permit distal movement of the extension member and release of the latch of the latch mechanism from engagement with the obturator sleeve.

Once the incision is made and as obturator tip 46 passes through the body tissue, the counterforce applied against obturator tip 46 by the body tissue ceases. Consequently, the absence of such counterforce permits compression spring 76 to spring distally, thereby biasing extension member 44 and obturator tip 46 distally to its distalmost position. In this position, conductive washer 140 and cutting knife 118 are not in electrical contact with conductive rod therefor 134. Thus, the circuit is interrupted thereby deenergizing conductive knife 118 and indicator light 132. With indicator light 132 non-illuminated, the surgeon is made aware that obturator tip 46 has penetrated the body tissue. As obturator tip 46 and extension member 44 move distally, lower leg 154 of pawl 102 engages the forward portion 152 of latch 98. In as much as further counter clockwise motion is prevented by stop pin 112, contact between lower leg 154 of pawl 102 and forward portion 152 of latch 98 causes the latch 98 to rotate counter clockwise around pin 100 and against the bias of lever spring 106 as shown in FIG. 10. This counterclockwise rotation of latch 98 results in counter clockwise rotation of rear engaging surface 108 thereby freeing the latch 98 from its engagement with internal shelf 181 of obturator sleeve 18.

As soon as latch 98 clears internal shelf 181, there no longer remains any restraint to the return of extension spring 52 (FIGS. 2 and 3) to its unloaded condition. Thus, trigger finger 48, obturator shaft 42, extension member 44 and obturator tip 46 are free to move proximally under the return force of extension spring 52. Obturator assembly 14 therefore assumes the initial position with obturator tip 46 within obturator sleeve 18, extension member 44 separated from obturator shaft 42 and pawl 102 distal of latch 98 as shown in FIGS. 4 and 7.

Figure 11:
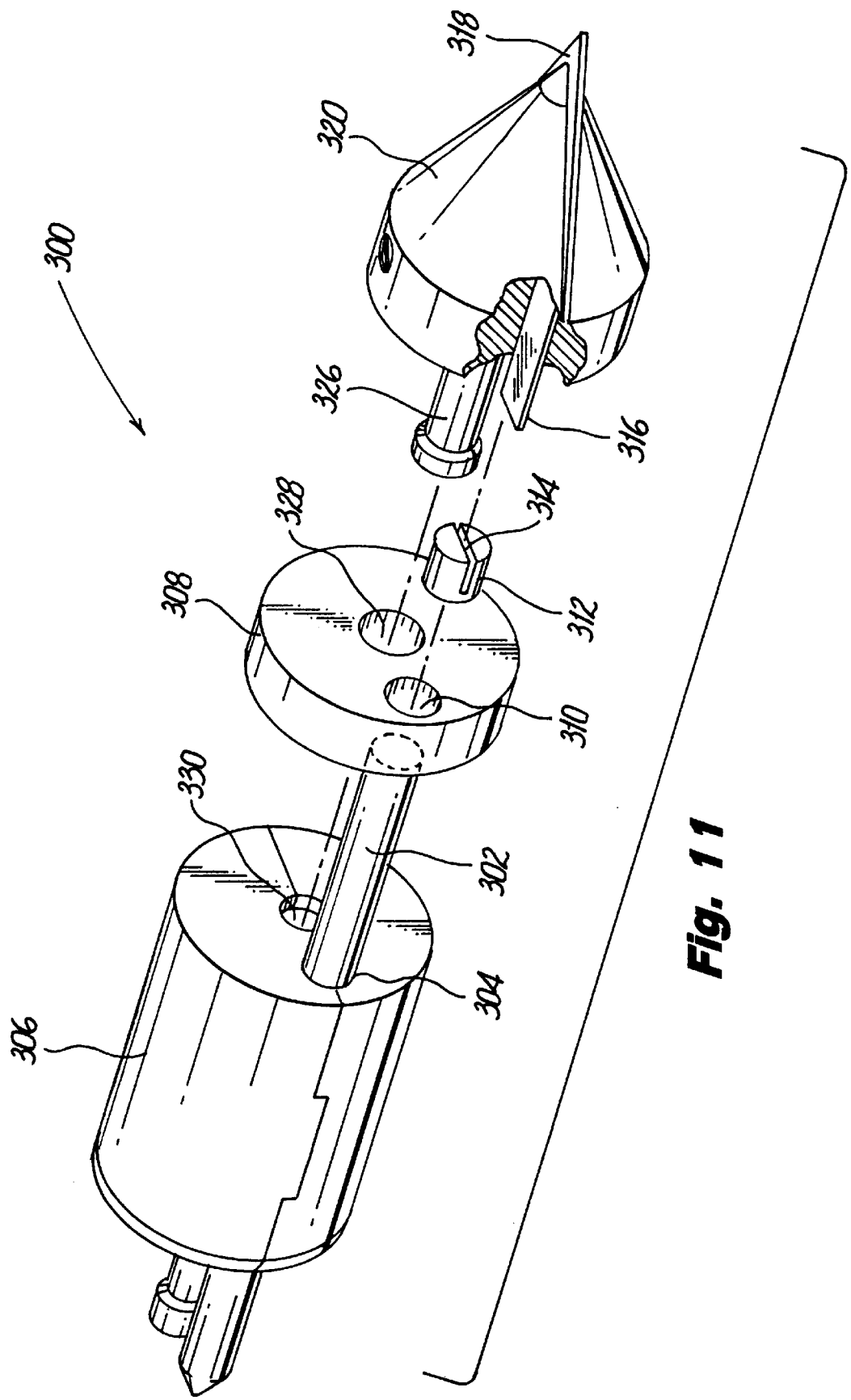
FIG. 11 a perspective view with parts separated of an alternative embodiment of the obturator portion of the trocar of FIG. 1.
Figure 12:
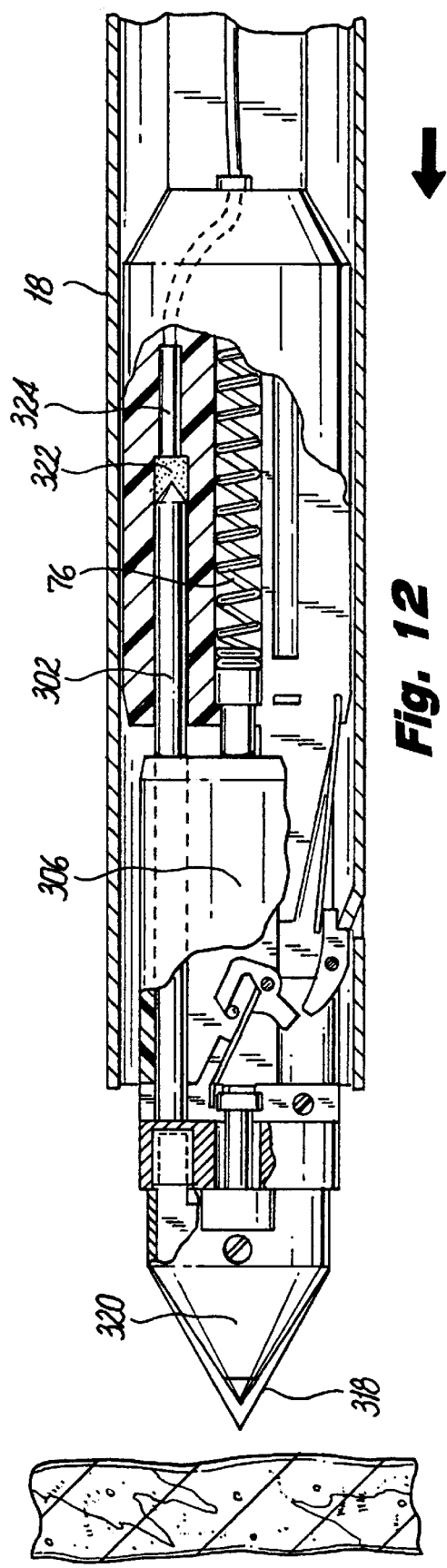
FIG. 12 is a side view in cross-section of the trocar of FIG. 11 illustrating the obturator tip in an extended position.
Figure 13:
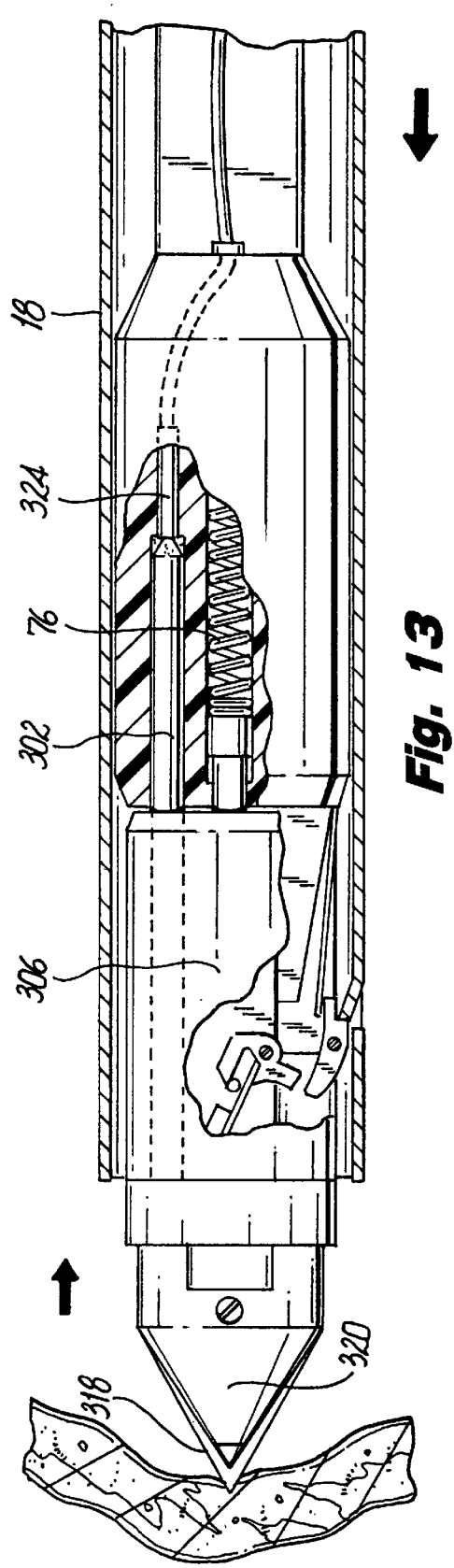
FIG. 13 is a side view in cross-section illustrating the trocar tip applied against tissue and the resulting proximal movement of the obturator tip.

Referring now to FIGS. 11–13, there is illustrated an alternate embodiment of the present disclosure. Obturatory assembly 300 is substantially similar in structure to the obturator of FIG. 1. However, in accordance with this embodiment, conductive rod therefor 302 is generally circular in cross-section and is fixedly secured within a longitudinal bore 304 of extension member 306. Conductive rod 302 also defines a greater cross-section than conductive rod 134 of the embodiment of FIG. 1. Conductive washer 308 defines a greater cross-section or thickness than that of the embodiment of FIG. 1 and includes a cylindrical aperture 310 to accommodate a corresponding cylindrically shaped connecting member 312. Connecting member 312 includes a slot 314 to accommodate single extension 316 of electrocautery cutting blade 318 and is conductive so as to "charge" the blade. Obturator tip 320 and conductive washer 308 are rotatably mounted to extension member 306 through tubular portion 326 which is integrally formed with the obturator tip and extends proximally therefrom. Tubular portion 326 is received within central aperture 328 of conductive washer 308 and aperture 330 of extension member 306 to effectuate the mounting in a manner similar to that described in connection with the embodiment of FIG. 1.

Obturator assembly 300 operates in a similar manner to assembly 14 of FIG. 1. With reference to FIG. 12, extension member 306 and obturator tip 320 are normally biased distally under the influence of compression spring 76. In this position, a gap 322 exists between the proximal end of conducting rod 302 and contact 324 of the electrocautery system. Thus, conductive knife 318 is not energized. With reference to FIG. 13, upon the application of conductive knife 318 against tissue, the counterforce supplied by the tissue causes obturator tip 320, extension member 306 and conducting rod 302 to move proximally whereby the proximal end of the conducting rod 302 engages the contact 324 to complete the circuit and energize the electrocautery knife 318.

As stated above, obturator tip 320 and conductive washer 308 are capable of rotating relative to extension member 306 to permit rotation of cutting blade 318 to facilitate the tissue penetration process. During rotation of these components, it is to be noted that the enlarged cross-section of conductor rod 302 provides a greater contacting surface area such that electrical contact is maintained with conductive washer 308.

While the above description contains many specifics, these specifics should not be construed as limitations on the scope of the invention, but merely as an exemplification of a preferred embodiment thereof. Those skilled in the art will envision other possible variations that are within the scope and spirit of the invention as defined by the claims appended hereto.

What is claimed is:

1. A trocar for penetrating a body wall, which comprises:
   a housing portion;
   obturator shaft at least partially extending from the housing portion and defining a longitudinal axis, the obturator shaft having proximal and distal ends;
   a conductor element connected to the obturator shaft and extending at least partially along the obturator shaft for conducting energy from an energy source; and
   a conductive tip member disposed adjacent the distal end of the obturator shaft for penetrating tissue, the conductive tip member mounted for axial movement relative to the obturator shaft between a first position to cause the conductive tip member to be in electrical communication with the conductor element and a second position to cause the conductive tip member to be electrically disassociated from the conductor element.

2. The trocar according to claim 1 comprising a biasing member operatively engageable at a proximal end thereof with the obturator shaft and at a distal end thereof with the conductive tip member, for biasing the conductive tip member to the second position thereof.

3. The trocar according to claim 2 wherein the conductive tip member is mounted to an extension member, the extension member mounted to the distal end of the obturator shaft and being reciprocally axially moveable relative to the obturator shaft to move the conductive tip member between the first and second positions thereof.

4. The trocar according to claim 2 wherein the biasing member includes a spring member.

5. The trocar according to claim 2 including an obturator sleeve mounted to the housing portion and extending distally therefrom.

6. The trocar according to claim 5 wherein the obturator shaft is reciprocally axially movable relative to the housing portion between a first position wherein the conductive tip member is positioned within the obturator sleeve and a second position wherein the conductive tip member is at least partially disposed beyond the obturator sleeve.

7. A trocar and cannula assembly, which comprises:
   a cannula assembly including a cannula defining an internal passageway therethrough; and a trocar assembly including:
  a housing portion;
  an obturator portion extending distally from the housing portion and being at least partially positionable within the internal passageway of the cannula, the obturator portion including:
    an obturator shaft mounted to the housing portion and having proximal and distal ends;
    a conductor element in mounted engagement with the obturator shaft and extending at least partially along the obturator shaft for conducting electrical energy from an electrical energy source; and
    an extension member connected to the distal end of the obturator shaft and having a conductive penetrating tip member associated therewith, the extension member being reciprocally longitudinally moveable relative to the obturator shaft between a first position which causes the conductive tip member to be in electrical communication with the conductor element and a second position which causes the conductive tip member to be electrically disassociated from the conductor element.

8. The trocar and cannula assembly according to claim 7 including a biasing member operatively engageable at a proximal end thereof with the obturator shaft and at a distal end thereof with the extension member, for biasing the extension member to the second position thereof.

9. The trocar and cannula assembly according to claim 7 including a conductor rod affixed to the obturator shaft and electrically connected to the conductor element wherein the conductive tip member is in electrical contact with the conductor rod upon movement of the extension member to the first position.

10. The trocar and cannula assembly according to claim 7 including a conductor rod affixed to the extension member and electrically connected to the conductive tip member, the conductor rod moveable with the extension member and being in electrical contact with the conductor element upon movement of the extension member to the first position.

11. The trocar and cannula assembly according to claim 7 wherein the penetrating tip member is mounted for rotational movement relative to the obturator shaft.

12. The trocar and cannula assembly according to claim 7 wherein the penetrating tip member is a conductive blade member.

13. The trocar and cannula assembly according to claim 7 further including an indicator mechanism associated with the conductor element for indicating when the penetrating tip member is in the first position thereof.

14. The trocar and cannula assembly according to claim 13 wherein the indicator mechanism includes a light.

15. The trocar and cannula assembly according to claim 7 wherein the obturator portion includes a support member for supporting the penetrating tip member, the support member being mounted to the extension member and having a recess for accommodating at least a portion of the penetrating tip member.

16. The trocar and cannula assembly according to claim 15 wherein the support member is mounted for rotational movement relative to the obturator shaft such that the penetrating tip member rotates therewith.

17. The trocar and cannula assembly according to claim 7 wherein the trocar assembly includes an obturator sleeve connected to and extending distally from the housing portion, the obturator portion being at least partially disposed within the obturator sleeve.

18. The trocar and cannula assembly according to claim 17 wherein the obturator shaft of the obturator portion is movement within the obturator sleeve between a retracted position wherein the penetrating tip member is contained within the obturator sleeve and an extended position wherein at least a portion of the penetrating tip member projects from a distal end of the obturator sleeve.

19. The trocar and cannula assembly according to claim 18 including means for releasably maintaining the obturator shaft in the extended position thereof.

20. The trocar and cannula assembly according to claim 19 wherein the means for releasably maintaining includes a latch mechanism, the latch mechanism including a latch member mounted to the obturator shaft and being configured and dimensioned to engage the obturator sleeve to maintain the obturator shaft in the extended position.

21. The trocar and cannula assembly according to claim 20 further including biasing means for biasing the obturator shaft to the retracted position thereof.

22. The trocar and cannula assembly according to claim 21 wherein the biasing means includes a spring member connected to the obturator shaft, the obturator shaft assuming the retracted position under influence of the spring member upon release of the latch member from the obturator sleeve.

23. The trocar and cannula assembly according to claim 20 wherein the latch mechanism includes a spring member, the spring member biasing the latch member into engagement with the obturator sleeve.

24. The trocar and cannula assembly according to claim 23 wherein the obturator sleeve includes an internal shelf portion, the latch member engageable with the internal shelf portion to maintain the obturator shaft in the extended position.

25. The trocar and cannula assembly according to claim 23 wherein the latch mechanism includes means for releasing the latch member from engagement of the latch member with the obturator sleeve.

26. The trocar and cannula assembly according to claim 25 wherein the releasing means includes a release member engageable with the latch member to move the latch member to a disengaged position disengaged from the obturator sleeve.

27. The trocar and cannula assembly according to claim 26 wherein the release member is configured and dimensioned to engage the latch member to move the latch member to the disengaged position upon movement of the extension member from the first position thereof to the second position thereof.

* * * * *